United States Patent [19]

Sizemore et al.

[11] Patent Number: 5,137,810

[45] Date of Patent: Aug. 11, 1992

[54] METHOD OF DETERMINING THE GRAM SIGN OF BACTERIA

[75] Inventors: Ronald K. Sizemore, Wilmington; Jerra J. Caldwell, Greensboro, both of N.C.

[73] Assignee: The University of North Carolina, Wilmington, N.C.

[21] Appl. No.: 343,493

[22] Filed: Apr. 26, 1989

[51] Int. Cl.$^5$ .............. G01N 33/554; G01N 33/569; G01N 33/53

[52] U.S. Cl. .................. 435/7.32; 435/7.1; 435/7.2; 435/7.9; 435/34; 435/7.8; 436/501; 436/827

[58] Field of Search .............. 435/7.1, 7.2, 7.32, 435/7.8, 34, 7.9; 436/501, 827

[56] References Cited

U.S. PATENT DOCUMENTS

| | | | |
|---|---|---|---|
| 4,298,689 | 11/1981 | Doyle et al. | 435/34 |
| 4,508,829 | 4/1985 | Sulitzeanu | 436/510 |
| 4,525,453 | 6/1985 | Guardino et al. | 435/34 |
| 4,592,994 | 6/1987 | Mattiasson | 435/7 |
| 4,596,769 | 6/1986 | Shockman et al. | 435/7 |
| 4,639,421 | 1/1987 | Sage, Jr. | 435/34 |
| 4,659,658 | 4/1987 | McCarthy et al. | 435/34 |
| 4,665,024 | 5/1987 | Mansour | 435/34 |
| 4,740,457 | 4/1988 | Parratt | 435/7 |
| 4,786,592 | 11/1988 | Deal et al. | 435/7 |
| 4,791,066 | 12/1988 | Ishiguro | 436/516 |

FOREIGN PATENT DOCUMENTS

57-26750 12/1982 Japan .

OTHER PUBLICATIONS

*Zinsser Microbiology*, (W. K. Joklik, et al., eds.) Appleton-Century-Crofts, E. Norwalk, Connecticut, pp. 24 and 32 (1984).
R. Sizemore et al., "Alternate Gram Staining Technique Using a Fluorescent Lectin," *Applied and Environmental Microbiology* 56, No. 7, 2245–2247 (1990).
H. Huy et al., *Chemical Abstracts* 85, No. 13, 451–452 (Abstract No. 92006n) (1976).
P. Allen et al., *Chemical Abstracts* 93, No. 5, 205 (Abstract No. 38232k) (1980).
F. Norbert et al., *Chemical Abstracts* 106, No. 5, 369 (Abstract No. 30955q (1987).
Seidl et al., *Biological Abstracts* 81, No. 1 (Abstract No. 7549) (1986).
M. Wagner, *Biological Abstracts* 70, No. 11 (Abstract No. 73741) (1980).
H. Morioka et al., *Biological Abstracts* 84, No. 10 (Abstract No. 99314) (1987).
Allen, A. K. et al., *Biochem. J.* 131, 155–162 (1973).
Astle, T., *Am. Clin. Prod. Rev.* 5, 24–25 (1986).
Atlas, R. M., "Use of Microbial Diversity Measurements to Assess Environmental Stress," (In M. J. Klug and C. A. Reddy (ed.), Current Perspectives in Microbial Ecology, American Society for Microbiology, Washington, D.C.), pp. 540–545 (1983).
Bartholomew, J. W., and Mittwer, T., *Bact. Rev.* 16, 1–29 (1953).
Gerhardt, P. (ed.), "Manual of Methods for General Bacteriology" (4th ed., American Society for Microbiology, New York) (1981).
Hucker, G. J., *J. Bact.* 6, 395–397 (1921).
Moriarity, D. J. W., and Hayward, A. C., *Microb. Ecol.* 8, 1–14 (1982).
Nagata, Y. and Burger, M., *J. Biol. Chem.* 249, 3116–3122 (1974).
Salton, M. R. J., "The Bacterial Cell Wall" (Elsevier, Amsterdam) (1964).
Sieburth, J. M., "Sea Microbes" (Oxford University Press, New York), p. 491 (1979).
Xu, Huai-Shu et al., *Microbial Ecology* 8, 313–323 (1982).

*Primary Examiner*—Esther L. Kepplinger
*Assistant Examiner*—Toni R. Scheiner
*Attorney, Agent, or Firm*—Bell, Seltzer, Park & Gibson

[57] ABSTRACT

A method of determining the gram sign of a bacterial sample is disclosed. In an embodiment of the method, the bacterial sample is first immobilized on a solid support. After immobilization, the bacterial sample is contacted to a peptidoglycan binding ligand (e.g., a ligand which selectively binds to N-acetylglucosamine). The ligand has a detectable label bound thereto. A preferred ligand is wheat germ agglutinin, and a preferred label is fluorescein. After being contacted to the ligand, the bacterial sample is washed with a wash liquid, the wash liquid being provided for a time effective to substantially remove the lectin from gram negative bacteria and ineffective to substantially remove the lectin from gram positive bacteria. The presence or absence of label bound to the bacterial sample is then detected. The presence of label bound to the sample indicates that bacteria in the sample are gram positive bacteria.

18 Claims, No Drawings

METHOD OF DETERMINING THE GRAM SIGN OF BACTERIA

BACKGROUND OF THE INVENTION

The gram stain is the most widely used taxonomic test of bacteria See P. Gerhardt, ed., *Manual of Methods for General Bacteriology* (4th ed. 1981). The technique is relatively simple, and in experienced hands gives reproducible results. The existing techniques do, however, have limitations. Most modifications of the gram stain, such as Hucker's, see G. Hucker, *J. Bact.* 6, 395 (1921), require at least four solutions and our staining steps. Furthermore, the stains used in the technique, particularly the primary stain, crystal violet, are concentrated and can be messy. The procedure is time consuming, with a single stain estimated to take approximately three minutes. K. Appel and M. Buschle, *Lab. Med.* 9, 149 (1985).

A variety of factors can produce erroneous results when using the conventional gram stain. See generally J. Bartholomew and T. Mittwer, *Bact. Rev.* 16, 1 (1953), K. Appel and M. Buschle, supra. P. Gerhardt, supra. For example, gram negative bacteria will appear as gram positive if decolorizing is incomplete or slide preparation results in a thick smear. Gram positive bacteria can also give false negative staining reactions, particularly when an old culture is used or decolorization is too extensive. Fortunately, these shortcomings are usually compensated for by the experience of bacteriologists. For as every instructor of bacteriology knows, training is essential for proper execution and interpretation of the gram stain.

Accordingly, objects of the present invention are to provide a new gram staining procedure which is simple, rapid, easy to interpret, resistant to errors, and requires few reagents.

SUMMARY OF THE INVENTION

A method of determining the gram sign of a bacterial sample is disclosed herein. In this method, the bacterial sample is contacted to a peptidoglycan binding ligand, the ligand having a detectable label bound thereto. Next, the bacterial sample is washed with a wash liquid, the wash liquid being provided for a time effective to substantially remove the ligand from gram negative bacteria and ineffective to substantially remove the ligand from gram positive bacteria. In the final step, the presence or absence of label bound to the bacterial sample is detected, the presence of label bound to the bacterial sample indicating that bacteria in the sample are gram positive bacteria.

The method of the present invention, in a preferred embodiment, takes advantage of the selective binding of a ligand to N-acetylglucosamine. K. Allen et al., *Biochem. J.* 113, 156 (1973), Y. Nagata and M. Burger, *J. Biol. Chem.* 249, 3116 (1974). N-acetylglucosamine is a prominent component of the peptidoglycan layer found in all eubacteria except Mycoplasma. Gram positive bacteria have their peptidoglycan layer in the outer portion of their cell wall. The exterior layer of gram negative bacteria is a membrane which covers the peptidoglycan layer. See, e.g., J. Salton, *The Bacterial Cell Wall* (1964). While ligands which bind N-acetylglucosamine have been used to identify gram negative bacteria, see U.S. Pat. No. 4,298,689 to Doyle et al., we nevertheless hypothesized that such a ligand would be able to attach to the peptidoglycan layer of gram positive bacteria, but would not be able to penetrate the outer membrane and would not be able to attach to the peptidoglycan layer of gram negative bacteria. While we do not wish the present invention to be bound to any particular theory of operation, it was our pursuit of this hypothesis which lead to the invention disclosed herein.

DETAILED DESCRIPTION OF THE INVENTION

In practicing the present invention, it is preferable to immobilize the bacterial sample on a solid support prior to the step of contacting the bacterial sample to a peptidoglycan binding ligand. Any solid support can be used, with exemplary solid supports including microscope slides, the interior wall of a well, the interior wall of a test tube, the interior wall of a cuvette, and beads. The solid support can be made of any conventional material, exemplary being glass, polyethylene, polystyrene, polypropylene, and cross-linked polysaccharides. Presently preferred is a glass microscope slide. Immobilization of the bacterial sample may be carried out by any suitable procedure, such as by heat fixation. In one particular embodiment of the invention, a bacterial sample is withdrawn from a human or animal host and immobilized on the solid support before substantial growth of the bacteria in the sample has occurred (that is, without subculturing the bacterial sample). In another particular embodiment of the invention, nonculturable bacteria (e.g., marine bacteria) are obtained from a native source (e.g., a marine environment) and immobilized on the solid support without an intervening culture step.

Peptidoglycan binding ligands include, for example, ligands which bind to N-acetylglucosamine, ligands which bind to N-acetylmuramic acid, and ligands which bind to diaminopimelic acid. Ligands which bind to N-acetylglucosamine are preferred. Ligands which can be used in practicing the present invention include both lectins and antibodies (monoclonal and polyclonal) which bind to the peptidoglycan layer of gram positive bacteria. Antibodies are obtained by known procedures. See, e.g., Milstein and Kohler, *Nature* 256, 495 (1975). Lectins which bind to N-acetylglucosamine are disclosed in Doyle et al. U.S. Pat. No. 4,298,689, the disclosure of which is incorporated herein by reference. These lectins include wheat germ lectin (i.e., wheat germ agglutinin), *Bandeirsea simplicifolia* lectin, and *Ulex europeus* lectin. Preferred as ligands are the lectins, with wheat germ agglutinin being particularly preferred. The source of wheat germ agglutinin is not critical, with sources such as kidney beans being suitable.

Labels which can be used in practicing the present invention include fluorescent labels, enzyme labels, and radioisotope labels. Exemplary fluorescent labels are fluorescein, rhodamine and auramine. Exemplary enzyme labels include peroxidase, B-glucuronidase, B-D-glucosidase, B-Dgalactosidase, urease, glucose oxidase plus peroxidase, galactose oxidase plus peroxidase, and acid phosphatase. Exemplary radioisotope labels are $^{14}C$, $^{125}I$, $^{131}I$, and $^{35}S$. Preferred are the fluorescent labels, with fluorescein particularly preferred.

The label is bound to the ligand by conventional procedures. See, e.g., Cronin et al., *Cytobios* 2, 225 (1970); Hunter and Greenwood, Nature 144, 945 (1962). Preferably, the label is covalently bound to the ligand.

We have found that best results with the present invention are obtained when the detecting step is carried out before the wash liquid has dried from the bacterial sample. Preferably, the wash liquid is an aqueous wash liquid. The bacterial sample may be brought in contact with either a continuous stream of wash liquid or a single aliquot of an excess quantity of wash liquid. The duration of the wash, which may vary somewhat between embodiments of the invention, is routinely determined through a few trials of the method. Generally, the wash time will be from about ten seconds to about thirty seconds in duration.

The detecting step can be carried out manually or automatically. The procedure chosen for carrying out the detection step will in turn influence the choice of label and solid support. Presently preferred is the detection of fluorescence from the bacterial sample, preferably by visual inspection of the bacterial sample under epifluorescent illumination. Those skilled in the art will, however, appreciate that the automation of gram staining procedures is a routine matter, see, e.g., K. Appel and M. Buschle, supra. and that the method of the present invention is particularly suited to automation.

Illustrative of gram positive bacteria which are identified by the method of the present invention are *Bacillus* species, Lactobacillus species, Micrococcus species, Mycobacterium species, Sporosarcina species, Stapyococcus species, and Streptococcus species. Illustrative of gram negative bacteria which are identified by the method of the present invention are cinetoacter species, Alcaligenes species, Cytophaga species, Enterobacter species, Escherichia species, Klebsiella species, Morganella species, Proteus species, Pseudomonas species, Rhodospirillum species, Salmonella species, Serratia species, and Shigella species.

The present invention will be explained in greater detail in the following examples. These examples are provided for illustrative purposes only, and are not to be taken as limiting of the invention.

EXAMPLE 1

Cultures

A total of 92 bacterial strains were tested. These strains consisted of isolates maintained in our laboratory and isolates identified by a local clinical laboratory. All strains were streaked to insure purity and were maintained for the duration of this study by periodic transfer to fresh tryptic soy agar slants (Difco Laboratories, Detroit, Michigan). Cultures were routinely grown at 35° C. Tables 1 and 2 below show the tentative identity of the strains used in this study.

TABLE 1

| Gram Positive Cultures Used | |
|---|---|
| Number of Strains Tested | Identity |
| 8 | *Bacillus* species |
| 2 | *Bacillus megaterium* |
| 1 | *Corynebacterium* species |
| 1 | *Lactobacillus acidophilus* |
| 1 | *Lactobacillus lactis* |
| 3 | *Micrococcus* species |
| 2 | *Micrococcus luteus* |
| 1 | *Mycobacterium smegmatis* |
| 1 | *Sporosarcina ureae* |
| 9 | *Staphylococcus aureus* |
| 7 | *Staphylococcus epidermidis* |
| 1 | *Staphylococcus saprophyticus* |
| 4 | *Streptococcus faecalis* |
| 2 | *Streptococcus mitis* |
| 4 | *Streptococcus pyogenes* |

TABLE 2

| Gram Negative Cultures Used | |
|---|---|
| Number of Strains Tested | Identity |
| 2 | *Acinetobacter calcoaceticus* |
| 2 | *Alcaligenes faecalis* |
| 1 | *Cytophaga* species |
| 1 | *Enterobacter aerogenes* |
| 5 | *Enterobacter cloacae* |
| 8 | *Escherichia coli* |
| 4 | *Klebsiella pneumoniae* |
| 1 | *Morganella morgani* |
| 2 | *Proteus mirabilis* |
| 4 | *Proteus vulgaris* |
| 1 | *Pseudomonas* species |
| 4 | *Pseudomonas aeruginosa* |
| 1 | *Pseudomonas fluorescens* |
| 1 | *Pseudomonas stutzeri* |
| 1 | *Rhodospirillum rubrum* |
| 1 | *Salmonella typhimurium* |
| 1 | *Serratia liquefaciens* |
| 4 | *Serratia marcescens* |
| 1 | *Shigella sonnei* |

EXAMPLE 2

Stains

Wheat germ agglutinin labeled with fluorescein isothiocyanate was purchased from Polysciences, Inc. of Warrington, Pennsylvania. This lectin was diluted to a concentration of 100 μg/ml with phosphate buffer containing 2.6 grams of $K_2HPO_4$ and 0.78 grams $Na_2CO_3$ per liter distilled water (pH 7.2). Aliquots of the diluted lectin solution could be stored frozen in the dark until needed. Stains for the conventional gram stains were prepared according to the Hucker's modification of the gram stain. P. Gerhardt, supra, G. Hucker, supra.

EXAMPLE 3

Staining Technique

Several variations were attempted, but the most successful, easily interpreted, and therefore preferred technique was performed as follows. Smears were made onto a glass slide using broth cultures directly or by mixing solid cultures from an agar surface in a drop of distilled water or the slide. After the smear air dried, the smears were heat fixed by quickly passing the slide through a flame. The heat fixed smear was then covered with a freshly thawed lectin solution. The lectin was left on the smear for 30 seconds and then gently washed off with phosphate buffer. A cover slip was then placed immediately on the wet slide. Optimal results were obtained only if the smear remained wet.

The smear was then observed at 400X using phase contrast to obtain proper focus. After the bacteria are in focus, the visible light is turned off, the epifluorescent illumination is turned on, and the smear is observed for fluorescence. The microscope used was an Olympus BHB with a fluorite 40X phase objective. For fluorescent microscopy, a BG12 exciter filter and a Y 475 barrier filter were used. Gram positive organisms fluoresce bright yellow green whereas gram negative bacteria do not fluoresce.

EXAMPLE 4

Technique Comparison

To test the validity of the technique, overnight cultures were randomly assigned numbers to insure anonymity and were stained as unknown cultures. Each organism was stained at least three separate times. Each numbered culture was also stained three times by a conventional Hucker's modification of the gram stain at the same time as the fluorescent stain. The results of the two techniques were then compared.

The two techniques were also compared using cultures grown for 48 hours, 72 hours, and six days.

The fluorescent gram stain technique proved to be a simple, quick (less than one minute), reliable technique. All but one of the gram positive organisms tested in this study fluoresced a bright yellow green after staining. With the exception of the species of the genus Pseudomonas, all the gram negative bacteria showed no fluorescence. The difference in fluorescence between the gram positive strains and the gram negative strains was very dramatic and the only strains showing intermediate results were the Pseudomonas species tested. With a little experience, we found it easy to recognize these strains among our numbered samples and to categorize these weak reactions as gram negative. The only other inconsistent result was a single strain of Coryneacterium which did not stain with the fluorescent stain.

In the 437 smears stained with the fluorescent lectin, only thirteen smears showed reactions which were different from the known gram reaction of the strain. In all but one of these cases, the gram reaction was incorrect for both gram techniques even though the techniques were run independently. These cultures were presumed to be contaminated. When some of these cultures were restreaked and reisolated, pure culture consistently gave the correct result. By comparison, 143 conventional gram stains were performed, with 27 giving inconclusive results and six giving incorrect results. With fresh pure cultures and a little experience, we found the results from the fluorescent technique to be more consistent and easier to read than the conventional stain procedure.

Culture age did not seem to effect the results of the fluorescent technique. One hundred percent of the 48 hour, 72 hour, and six day cultures showed consistent fluorescent staining results. However, with the conventional gram stains, in the 48 hour cultures 50% of the gram positive strains appeared gram negative, and most of the 72 hour (83%) and six day (86%) gram positive cultures appeared negative.

The simplicity and hardiness of this technique surprised us. We found that the wet smear covered with a coverslip gave the brightest result and was the simplest way to perform the stain. A counterstain included in the lectin mixture would give contrast to the cell in the smear and thus avoid the use of phase contrast optics for the initial observation of the cells. However, many of the stains tested with the lectin masked the fluorescence and gave false negative results. We soon came to the conclusion that the small amount of resolution lost using the fluorite phase objective for fluorescent microscopy was insignificant. However, care should be taken to use an objective, such as one made of fluorite glass, which is suitable for fluorescent microscopy.

One of the most exciting features of this technique is the insensitivity of the technique to the age of the culture. This implies that this technique can be applied directly to specimens without culturing the bacteria in the specimen. For example, clinical specimens with high bacterial loads can be stained and observed directly. This could be particularly helpful with fastidious, slow growing and/or anaerobic bacteria Furthermore, from the results obtained, an antibiotic can be prescribed which is appropriate for either a gram negative or gram positive infection. A more likely application of this technique is to analyze viable but nonculturable microorganisms. See H. Xu et al., *Microb. Ecol.* 8, 313 (1982). As an example, marine bacteria are reported to be 70-90% gram negative, D. Moriarity and A. Hayward, *Microb. Ecol.* 8, 1 (1982); J. Sieburth, *Sea Microbes* 491 (1979), but this result comes from cultured marine bacteria. Since most marine bacteria cannot be cultured on media, see R. Atlas, in M. Klug and C. Reddy (eds.), *Current Perspectives in Microbial Ecology,* 540-545 (1983), this technique could be used to give a better indication of the actual bacterial composition in the environment.

The foregoing examples are illustrative of the present invention, and are not to be taken as limiting thereof. The invention is defined by the following claims, with equivalents of the claims to be included therein.

That which is claimed is:

1. A method of determining the gram sign of a bacterial sample, comprising:
    (a) contacting said bacterial sample to a lectin which selectively binds to N-acetylglucosamine, said lectin having a detectable label bound thereto; then
    (b) washing said bacterial sample with a wash liquid, said wash liquid being provided for a time effective to substantially remove said lectin from gram negative bacterial and ineffective to substantially remove said lectin from said gram positive bacterias; and then
    (c) detecting the presence or absence of label bound to said bacterial sample, the presence of label bound to said sample indicating that bacteria in said sample are gram positive bacteria.

2. A method according to claim 1, wherein said lectin is wheat germ agglutinin.

3. A method according to claim 1, wherein said label is selected from the class consisting of fluorescent labels, enzyme labels, and radioisotope labels.

4. A method according to claim 1, wherein said label is a fluorescent label.

5. A method according to claim 1, wherein said label is fluorescein.

6. A method according to claim 1, wherein said label is covalently bound to said lectin.

7. A method according to claim 2, wherein said label is fluorescein, and said label is covalently bound to said lectin.

8. A method according to claim 1, wherein said wash liquid is an aqueous liquid.

9. A method according to claim 1, wherein said detecting step is carried out before said wash liquid has dried from said bacterial sample.

10. A method according to claim 1, further comprising the step of immobilizing said bacterial sample on a solid support prior to said step of contacting said bacterial sample to said lectin.

11. A method according to claim 10, wherein said lectin is wheat germ agglutinin.

12. A method according to claim 11, wherein said label is fluorescein, and said label is covalently bound to said wheat germ agglutinin.

13. A method of confirming the presence of gram positive bacteria, comprising:
    (a) immobilizing said gram positive bacteria on a solid support; then (b) contacting said gram positive bacteria to wheat germ agglutinin having a detectable label bound thereto; then (c) washing said gram positive bacteria with a wash liquid, said wash liquid being provided for a time ineffective to substantially remove said wheat germ agglutinin from said gram positive bacteria; and then, before said wash liquid has dried from said gram positive bacteria, (d) detecting the presence of label bound to said gram positive bacteria, the presence of said label confirming said gram positive bacteria as gram positive bacteria.

14. A method according to claim 13, wherein said label comprises fluorescein, and said wheat germ agglutinin is covalently bound to said label.

15. A method according to claim 14, wherein said gram positive bacteria is selected from the class consisting of Bacillus species, Lactobacillus species, Micrococcus species, Mycobacterium species, Sporosarcina species, Staphylococcus species, and Streptococcus species.

16. A method of conforming the presence of gram negative bacteria, comprising:

(a) immobilizing said gram negative bacteria on a solid support; then (b) contacting said gram negative bacteria to wheat germ agglutinin having a detectable label bound thereto; then (c) washing said gram negative bacteria with a wash liquid, said wash liquid being provided for a time effective to substantially remove said wheat germ agglutinin from said gram negative bacteria; and then, before said wash liquid has dried from said gram negative bacteria, (d) detecting the presence of label bound to said gram negative bacteria, the absence of said label confirming said gram negative bacteria as gram negative bacteria.

17. A method according to claim 16, wherein said label comprises fluorescein, and said wheat germ agglutinin is covalently bound to said label.

18. A method according to claim 17, wherein said gram negative bacteria is selected from the class consisting of Acinetobacter species, Alcaligenes species, Cytophaga species, Enterobacter species, Escherichia species, Liebsiella species, Morganella species, Proteus species, Pseudomonas species, Rhodospirillum species, Salmonella species, Serratia species, and Shigella species.

* * * * *

UNITED STATES PATENT AND TRADEMARK OFFICE
CERTIFICATE OF CORRECTION

PATENT NO. : 5,137,810

DATED : 11 August 1992

INVENTOR(S) : Ronald K. Sizemore and Jerra J. Caldwell

It is certified that error appears in the above-identified patent and that said Letters Patent is hereby corrected as shown below:

Column 3, line 24-25, please change "Stapyococcus" to read --Staphylococcus--.

Column 3, line 28, please change "cinetoacter" to read --Acinetobacter--.

Column 5, line 21, please change "Coryneacterium" to read --Corynebacterim--.

Column 6, line 29, Claim 1, please change "bacterial" to read --bacteria--.

Column 6, line 30, Claim 1, please change "bacterias" to read --bacteria--.

Column 7, line 26, Claim 16, please change "conforming" to --confirming--.

UNITED STATES PATENT AND TRADEMARK OFFICE
CERTIFICATE OF CORRECTION

PATENT NO. : 5,137,810
DATED : August 11, 1992
INVENTOR(S) : Ronald K. Sizemore, and Jerra J. Caldwell It is certified that error appears in the above-indentified patent and that said Letters Patent is hereby corrected as shown below:

Column 8, line 23, Claim 18, please change "Liebsiella" to read --Klebsiella--.

Signed and Sealed this

Twelfth Day of October, 1993

Attest:

BRUCE LEHMAN

*Attesting Officer*     *Commissioner of Patents and Trademarks*